United States Patent [19]
Caillouette

[11] Patent Number: 6,066,124
[45] Date of Patent: May 23, 2000

[54] CONTROL OF TREATMENT FLUID APPLICATION TO TISSUE

[76] Inventor: James C. Caillouette, 685 Oak Knoll Cir., Pasadena, Calif. 91106

[21] Appl. No.: 09/199,208

[22] Filed: Nov. 24, 1998

[51] Int. Cl.[7] .......................... A61M 31/00; A61M 35/00
[52] U.S. Cl. ............................. 604/514; 604/515; 604/3
[58] Field of Search ................................. 604/1–3, 500, 604/271, 514, 515

[56] References Cited

U.S. PATENT DOCUMENTS

| | | |
|---|---|---|
| 5,738,634 | 4/1998 | Caillouette . |
| 5,782,801 | 7/1998 | Caillouette . |
| 5,827,200 | 10/1998 | Caillouette . |

*Primary Examiner*—Ronald Stright, Jr.
*Assistant Examiner*—Kelly M. Cheney
*Attorney, Agent, or Firm*—William W. Haefliger

[57] ABSTRACT

The method of applying screening or treatment fluid to tissue, and employing an elongated carrier, having a first end portion; a flexible outer container having a generally tubular second end portion and a frangible inner container protectively located within the outer container, there being screening or treatment fluid within the inner container, and a fluid applicator carried by the flexible outer container, to communicate with the interior of the outer container which includes a connector having a body defining oppositely projecting third and fourth end portions, and interfitting the third and fourth end portions with the first and second end portions, respectively, so that the elongated carrier is substantially rigidly joined to first end portion of the flexible outer container, exerting pressure on a pressure application region of the outer container spaced from the connector body, and sufficient to rupture the inner container, thereby releasing screening or treatment fluid into the interior of the outer container, enabling fluid migration to the applicator; and manipulating the elongated carrier thereby to manipulate the outer container when inserted into the body cavity, and by force transmission via the connector body, to cause the applicator to controllably apply screening or treatment fluid to tissue in a cavity.

36 Claims, 4 Drawing Sheets

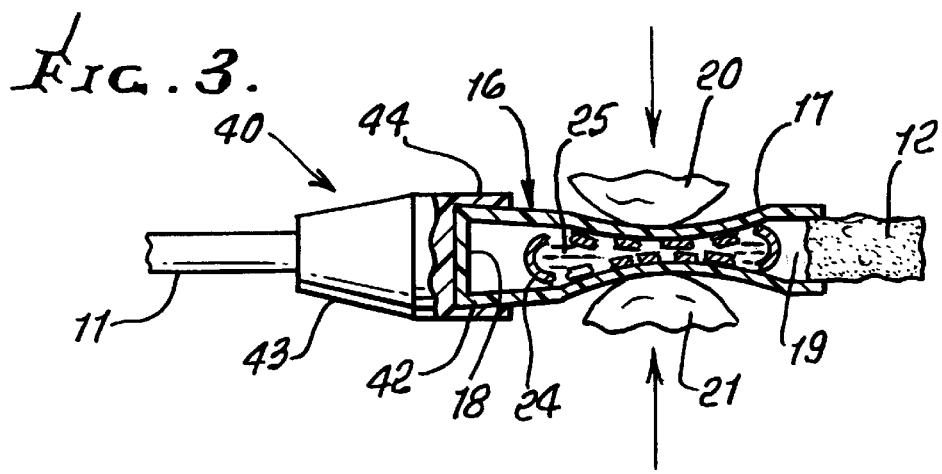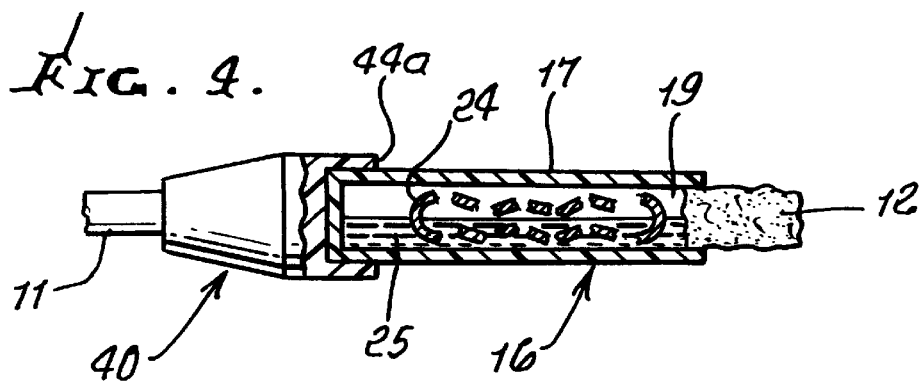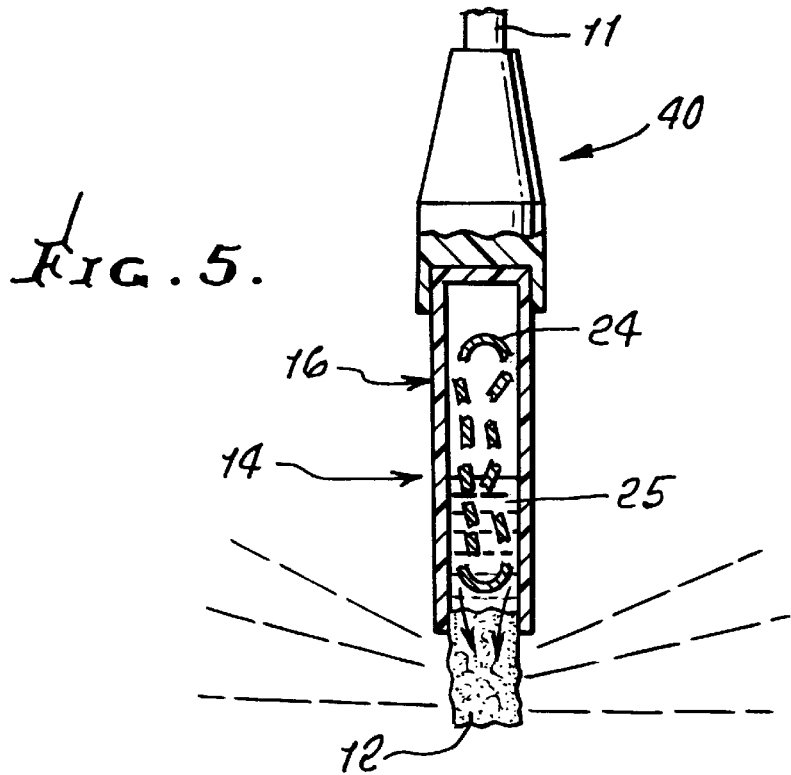

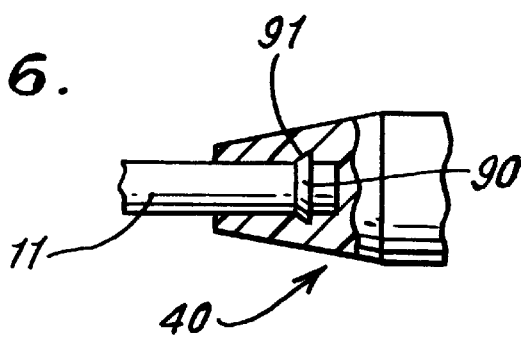
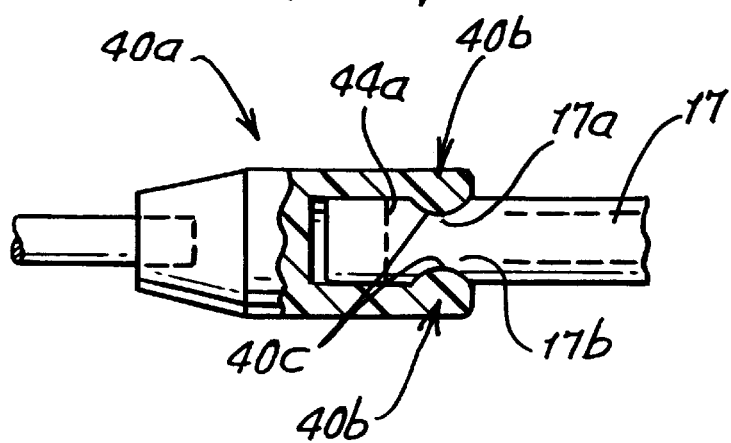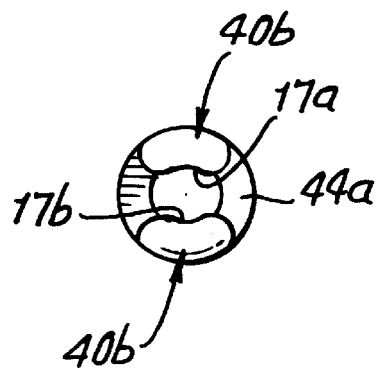
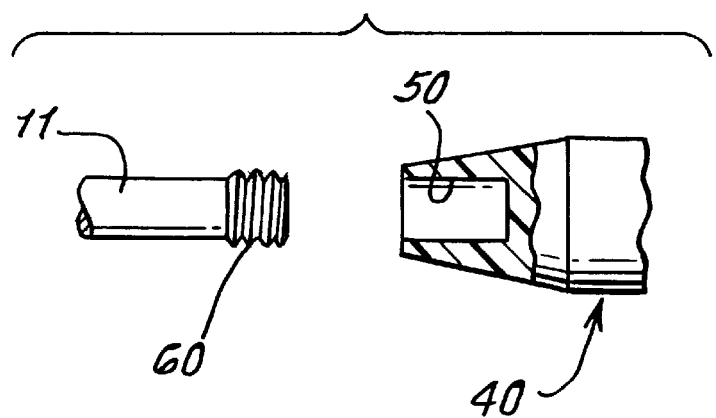

CONTROL OF TREATMENT FLUID APPLICATION TO TISSUE

BACKGROUND OF THE INVENTION

This invention relates generally to screening or treatment of body parts, and more particularly to method and apparatus for easily and quickly applying treatment fluid to tissue such as that of the cervix, vagina, or vulva as well as other body parts which may normally be concealed.

There is need for simple, easily used apparatus for reliably and quickly applying screening or treatment fluid or liquid to body parts, for example, the cervix. Such fluid may be test fluid for use in cancer detection. There is also need for simple, effective methods to locally apply such fluids. Prior apparatus and techniques were cumbersome, and lacked the unusual advantages disclosed herein. Fluids used may degrade quickly after being exposed to air.

SUMMARY OF THE INVENTION

It is a major object of the invention to provide improvements in method and apparatus meeting the above needs. Basically, the method of the invention employs:

a) an elongated carrier, having a first end portion, b) a flexible outer container having a generally tubular second end portion and a frangible inner container protectively located within the outer container, there being screening or treatment fluid within the inner container, and a fluid applicator carried by the flexible outer container, to communicate with the interior of the outer container, and the method includes the following steps:

c) providing a connector having a body defining oppositely projecting third and fourth end portions, d) interfitting said third and fourth end portions with said first and second end portions, respectively, so that said elongated carrier is substantially rigidly joined to said second end portion of the flexible outer container, e) exerting pressure on a pressure application region of said outer container spaced from said connector body, and sufficient to rupture the inner container, thereby releasing said screening or treatment fluid into the interior of the outer container, enabling fluid migration to the applicator, f) and manipulating said elongated carrier thereby to manipulate said outer container, and by force transmission via said connector body, to cause said applicator to controllably apply said screening or treatment fluid to said tissue.

As will be seen, the fourth end portion on the body may be telescopically interfitted with said second end portion in said flexible outer container, and retained in interfitted connection; and the third end portion on the body may be telescopically interfitted with said first end portion on said elongated carrier, and retained in interfitted condition. Further, the telescopic interfitting of said fourth end portion on said body with said second end portion on said flexible outer container is established at locations that are everywhere spaced from said pressure application region of said outer container.

It is another object to provide the connector body in molded form to have one of the following:

i) synthetic resinous composition ii) rubber composition.

A further object is to provide the connector body to have opposite end recesses at said third and fourth end portions thereof. Such opposite end recesses may be advantageously provided in cylindrical form and to have a relatively smaller diameter at said third end portion, and a relatively larger diameter at said fourth end portion.

The basic apparatus of the invention includes:

i) a connector having a body defining oppositely projecting third and fourth end portions, ii) said third and fourth end portions being interfitted with said first and second end portions, on the carrier and the container, respectively, so that said elongated carrier is substantially rigidly joined to said first end portion of the flexible outer container, iii) whereby pressure may be exerted on a pressure application region of said outer container spaced from said connector body, and sufficient to rupture the inner container, thereby releasing said screening or treatment fluid into the interior of the outer container, enabling fluid migration to the applicator, iv) and whereby said elongated carrier may be manipulated thereby to manipulate said outer container when inserted into the body cavity, and by force transmission via said connector body, to cause said applicator to controllably apply said screening or treatment fluid to said tissue in said cavity.

Means may be provided to assure releasable gripping or positive gripping of the connector to the carrier and to the outer container, in assembled sequence, for safe manipulative use, and for later separate disposal after use.

These and other objects and advantages of the invention, as well as the details of an illustrative embodiment, will be more fully understood from the following specification and drawings, in which:

DRAWING DESCRIPTION

FIG. 3 is a view like FIG. 2 showing manual fracture or rupture of an inner container located within an outer container, as also seen in FIG. 2;

FIG. 4 is a view like FIG. 3 showing liquid from the inner container having been released into the interior of the outer container;

FIG. 5 is a view like FIG. 4 the fluid or liquid having flowed from the interior of the outer container to an applicator such as a swab at the end of the assembly, for use in applying such fluid or liquid to any body part surface, such as the cervix; and FIG. 6 is a view like FIG. 2 showing a modification;

FIGS. 7 and 8 are side and end views of a grip facilitating modification;

FIG. 9 is a side elevation showing another grip facilitating modification;

DETAILED DESCRIPTION

Figure 1:
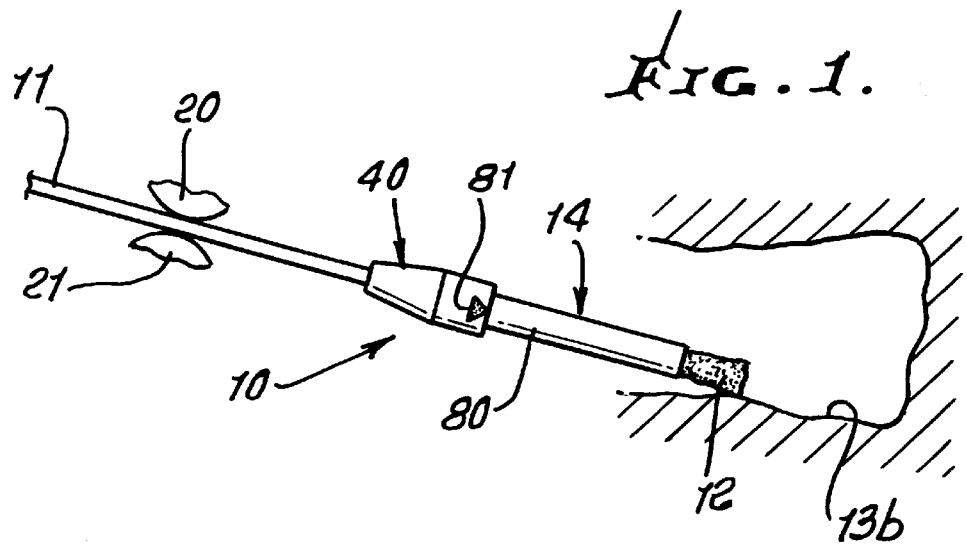
FIG. 1 is a view showing use of an elongated assembly incorporating the invention.

In FIG. 1 an elongated assembly 10 is shown to include an elongated carrier 11 such as a stick, and an applicator such as a swab 12. The applicator may comprise a sponge, or other porous material, at the forward end of the assembly. The applicator is used to locally apply fluid to a concealed body surface, such as the surface 13b of the cervix, during use of the assembly. FIG. 1 shows a user's finger and thumb 20 and 21 manipulating the assembly. The applicator may be used for fluid application to the vagina or vulva.

Controllable screening or treatment liquid supply means is provided at 14, between the forward end of the carrier 11 and the applicator 12. The test means 14 is adapted to be manually squeezed to effect controllable communication of contained liquid to the applicator or swab 12, for applying such liquid as to a local area or areas such as the cervix or vagina. Since the supply means or unit 14 is located between 11 and 12, it provides a test means incorporated in or on the assembly 10.

Figure 2:
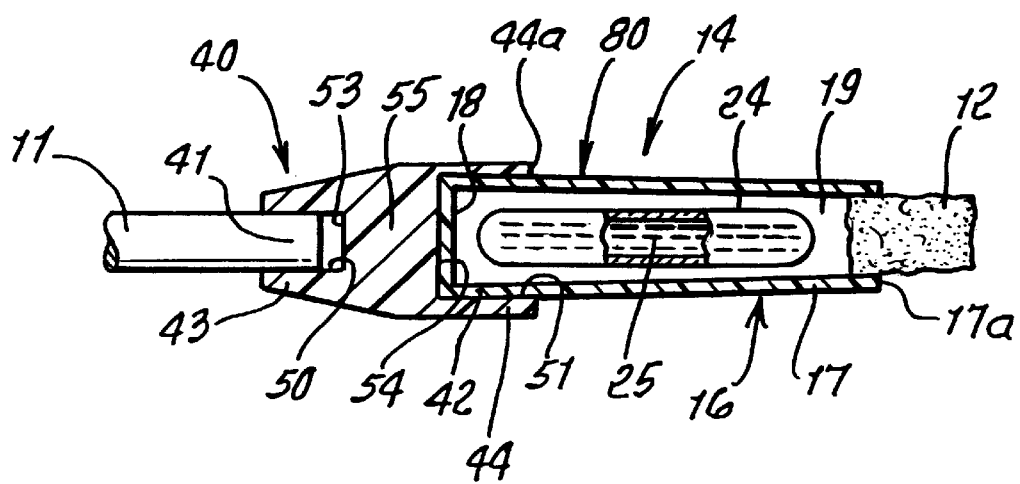
FIG. 2 is an enlarged section taken lengthwise through a connector region of the FIG. 1 assembly.
Figure 2A:
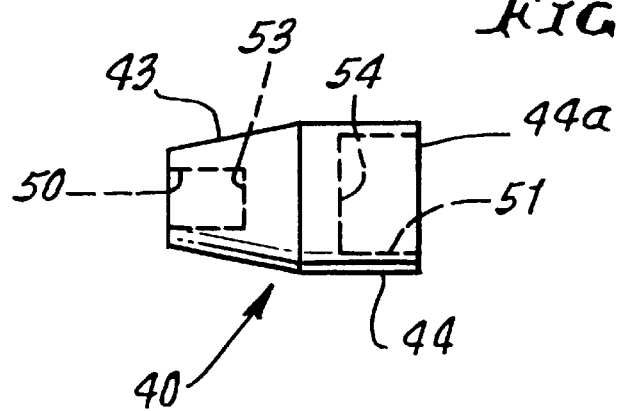
FIG. 2a is a side view of a connector body as also is seen in FIG. 2.

FIG. 2 shows the means or unit 14 as incorporating an outer container 16 which is elongated and tubular, having cylindrical side wall 17, and end wall 18, connected via body 40 to the forward end of carrier 11 such as a stick. Connector 40 is typically molded to be rigid or substantially rigid, and consists of one of the following:

i) synthetic resin
ii) elastomeric material

The interior 19 of the container communicates with applicator or swab 12 and for this purpose the swab may be received into the open forward end portion 17a of the outer container, thereby mounting the swab to the container.

A frangible inner container 24 is located within the interior 19 of container 16, and may be elongated, as shown. Container 24 may consist of a hollow, thin-walled glass capsule to contain liquid 25. The outer container side wall 17 may consist of relatively stiff plastic material, which is sufficiently flexible to be squeezed, as by between user's finger and thumb 20 and 21, as seen in FIG. 3. Such squeezing, exerting pressure on the outer container, is sufficient to rupture the inner container as seen in FIG. 3, thereby releasing contained liquid 25 into the interior 19 of the outer container. See FIG. 4. This provides for controlled access of the treatment liquid to the swab, for application, as seen in FIG. 1. See also FIG. 5 orientation of the assembly 10 to cause gravitation of the liquid to flow into contact with the end of applicator of swab carried by the forward end portion of the outer container. One can control the load of solution in the swab by squeezing of the plastic container tube. For example, squeeze enough to saturate the swab and repeat as needed to keep a satisfactory level of saturation but no drip.

Whereas the carrier stick may be characterized as having a first end portion 41, the flexible outer container 16 may be characterized as having a generally tubular second end portion 42. The connector body 40 is characterized as defining oppositely projecting third and fourth end portions 43 and 44 which are interfitted with the first and second end portions 41 and 42 respectively so that said elongated carrier is substantially rigidly joined to said second end portion of the flexible outer container. Further, the fourth end portion 44 is telescopically interfitted with said second end portion of said flexible outer container, and retained in interfitted connection. This enables quick, positive, assembly of the three components, when needed, and easy manipulation of the carrier remotely from the applicator, during use. Use of standard containers 24 is thereby afforded, without modifications.

Further, telescopic interfitting of said fourth end portion on said body with said second end portion on said flexible outer container is established at locations that are everywhere spaced from said pressure application region 80 of said outer container. Edge 44a of 44 may demark the edge of region 80; and an indicator such as an arrow 81 on 44 may further indicate the zone of pressure application. End portion 44 of 40 firmly grips container end portion 42, during flexing of 24, as seen in FIG. 3.

Note that the connector body has opposite end recesses 50 and 51 at the referenced third and fourth end portion locations. Such recesses are provided in cylindrical form and to have a relatively smaller diameter at said third end portion, and a relatively larger diameter at said fourth end portion. Inner end walls 53 and 54 of the recesses are spaced apart by interior wall 55, as shown, to provide rigidity to the connector body, enhancing its manipulative utility, and blocking bending of the body.

FIG. 6 shows provision of interfitting tongue and groove parts 90 and 91 on 11 and 40 for positive retention of the body to elongated carrier 11. Such parts block separation of the body and carrier, and they interfit upon endwise assembly of the body and carrier. Adhesive may be used to bond the interfitting elements 10 and 40, and 40 and 24.

The screening liquid may consist of aqueous iodine solution, known as Lugol's or Shiller's solution, for reaction , as with the surface of the cervix. Such treatment causes a local discoloration of all normal tissue if no cancer cells are present, which may be observed by the physician. Normal tissue contains glycogen—abnormal tissue does not (glygogen is a sugar). Iodine combines with tissue glycogen to cause a dark mahogany stain on normal tissue. Abnormal tissue does not stain with iodine solution. The user may thereby quickly and efficiently determine the existence of cervical pre-cancer or cancer, using a simple unitary screening test means and procedure as described, readily accessible to the cervix just after iodine release from storage. Another usable solution for this purpose consists of 10 parts Iodine, 30 parts Potassium Iodide and 350–500 parts distilled water. Acetic acid solution may be employed, as referred to above.

After such use, the carrier or stick is then disposable. Note that screening or treatment liquid is easily applied to a concealed body part or surface, without the user's fingers coming in contact with the screening liquid, such as iodine.

The apparatus may be used for treatment, as for example where treatment fluid such as podophyllum is released from the fractured inner container for application via the swab to treat human papilloma virus.

Referring to FIGS. 7 and 8, the modified connector 40a has at least one grip 40b, and preferably two such grips 40b, projecting rightwardly beyond edge 44a, as shown, and adjacent side wall portions 17a and 17b of the flexible, thin walled container 17. The grips have bulged inner walls 40c that grip the side wall portions 17a and 17b, depressing them inwardly toward one another, whereby the connector 40a has a positive grip connection to the container 17. also, the grip terminals serve as indicators, showing approximately where the user should grasp the container 17 to deflect it as in FIG. 3. Endwise ready separation of 40 and 17 is enabled, for separate safe disposal of same, after use.

Figure 10:
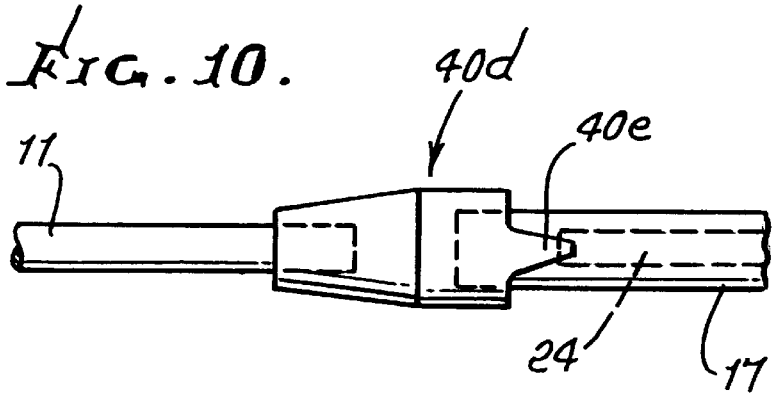
FIGS. 10 and 11 are top and side views of a modification employing an indicator.
Figure 11:
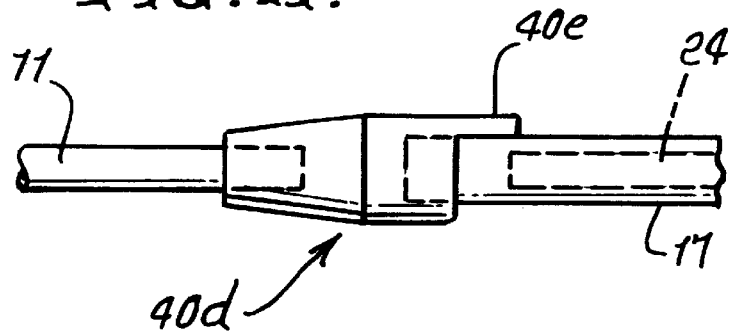

FIGS. 10 and 11 show a modified connector 40d like that of FIG. 2; however, a rightward projection 40e has a terminal that serves as an indicator, showing approximately where the user should grasp the container 17 to deflect it, as in FIG. 3.

FIG. 9 shows serrations 60 on the side of the carrier 11, and adapted and sized to interferingly engage the bore 50 of the connector 40 when 11 is endwise assembled to 40. The serrations tend to bite into the bore, as they are typically harder than the material of the connector 40, providing a positive grip. Such serrations can be used in any of the forms of the invention seen in FIGS. 2, 2a, 7 and 8, and 9 and 10. Endwise ready separation of 17 and 11 is thereby enabled, for separate, safe disposal of same, after use.

Figure 12:
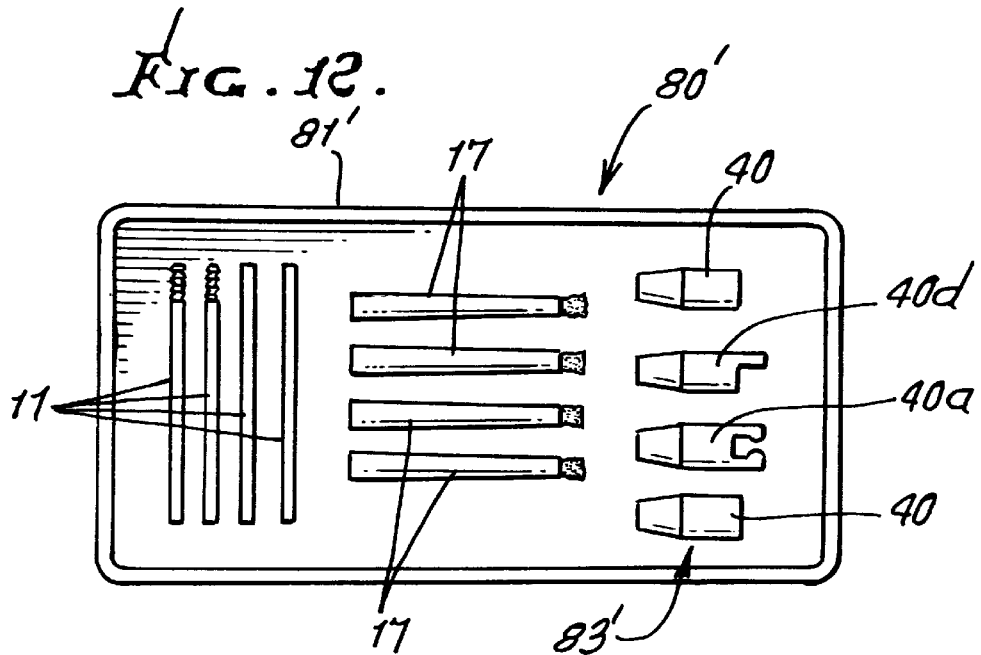
FIG. 12 is a plan view of a kit for elements to be selectively assembled.

FIG. 12 shows a kit 80' including a portable container 81' in which multiple of the carriers (same as 11); flexible outer containers (same as 17); and connectors are received. The connectors may have the configuration and construction of any of those described herein, or equivalents of same. The connectors seen at 83' in the kit may take any such forms.

The physician user is benefitted by the ability to remove from the kit, and on an as-needed basis, selected carriers, containers and connectors, to be selectively endwise interfitted as described herein, to produce the manipulable operative assembly of three components, to suit his purposes.

I claim:

1. In the method of applying screening or treatment fluid to tissue, and employing:
   a) an elongated carrier, having a first end portion,
   b) a flexible outer container having a generally tubular second end portion and a frangible inner container protectively located within the outer container, there being screening or treatment fluid within the inner container, and a fluid applicator carried by the flexible outer container, to communicate with the interior of the outer container, the steps that include:
   c) providing a connector having a body defining oppositely projecting third and fourth end portions,
   d) and interfitting said third and fourth end portions with said first and second end portions, respectively, so that said elongated carrier is substantially rigidly joined to said second end portion of the flexible outer container,
   e) exerting pressure on a pressure application region of said outer container spaced from said connector body, and sufficient to rupture the inner container, thereby releasing said screening or treatment fluid into the interior of the outer container, enabling fluid migration to the applicator,
   f) and manipulating said elongated carrier thereby to manipulate said outer container, and by force transmission via said connector body, to cause said applicator to controllably apply said screening or treatment fluid to said tissue in said cavity.

2. The method of claim 1 wherein said tissue is one of the following:
   i) cervical tissue
   ii) vaginal tissue
   iii) other human body tissue.

3. The method of claim 1 wherein said fourth end portion on said body is telescopically interfitted with said second end portion of said flexible outer container, and retained in interfitted connection.

4. The method of claim 3 wherein said telescopic interfitting of said fourth end portion on said body with said second end portion on said flexible outer container is established at locations that are everywhere spaced from said pressure application region of said outer container.

5. The method of claim 1 wherein said third end portion on said body is telescopically interfitted with said first end portion on said elongated carrier, and retained in interfitted condition.

6. The method of claim 5 including providing a tongue and groove locking means associated with said, third and first end portions for blocking separation of said body and carrier after interfitting thereof.

7. The method of claim 1 wherein said connector body is provided in molded form to have one of the following:
   i) synthetic resinous composition
   ii) rubber composition
   iii) elastomeric material.

8. The method of claim 7 wherein said connector body is provided to have opposite end recesses at said third and fourth end portions thereof.

9. The method of claim 8 wherein said opposite end recesses are provided in cylindrical form and to have a relatively smaller diameter at said third end portion, and a relatively larger diameter at said fourth end portion, and a rigid wall is provided between said recesses to prevent bending of said body.

10. The method of claim 1 wherein said screening or treatment fluid consists essentially of one of the following:
    i) an aqueous iodine solution,
    ii) an acetic acid solution,
    iii) podophyllum treatment fluid,
    iv) other diagnostic or treatment fluid.

11. The method of claim 10 including thereafter observing the tissue to determine tissue color change indicating pre cancer or cancer cells' presence in the unchanged area, and wherein normal tissue becomes a mahogany color while pre cancerous or cancerous tissue remains substantially unchanged.

12. The method of claim 1 wherein said outer container is provided in relatively close association with said applicator.

13. The method of claim 1 wherein said pressure is exerted manually, at a region on the container demarked by an edge defined by body.

14. The method of claim 13 including controlling said manual pressure to control fluid flow to the applicator.

15. The method of claim 13 including controlling said manual pressure to control the amount of screening or treatment fluid flow to the applicator.

16. The method of claim 13 including inserting said applicator into end of said outer container.

17. The method of claim 1 including manipulating said assembly to cause the connector body to exert endwise and sidewise force on the outer container, causing the outer container to exert endwise and sidewise force on the applicator to cause the applicator to apply screening or treatment fluid to said tissue.

18. The method of claim 1 wherein said outer container is provided to consist of thin-walled flexible plastic material, and said inner container consists of glass.

19. The method of claim 1 wherein said applicator is provided to be carried by the outer container.

20. The method of claim 1 including providing means in the connector to grip and thereby deflect a side wall defined by the flexible outer container.

21. The method of claim 20 wherein said means is provided by locating at least one grip having an inner wall protrusion locally engaging said side wall defined by the flexible outer container.

22. The method of claim 1 including providing means on one of the connectors and carrier to locally grip the other of the connector and carrier.

23. The method of claim 22 including locating said serrations at the side of the carrier to grip a bore formed by the connector.

24. The method of claim 1 including providing an indicator at one end of the connector to become positioned proximate a zone of the flexible outer container to be squeezed for fracturing said inner container.

25. The method of claim 24 wherein said indicator is provided to locally project lengthwise of and adjacent a side wall of the flexible outer container.

26. The method of claim 1 that includes providing multiple of said carriers, flexible outer containers, and connectors in a kit, and removing from the kit, on an as needed basis, selected carriers, containers and connectors, to be interfitted as defined in claim 1.

27. An apparatus for applying screening or treatment fluid to body tissue, said apparatus including:
   a) an elongated carrier, having a first end portion,
   b) a flexible outer container having a generally tubular second end portion and a frangible inner container protectively located within the outer container, there being screening or treatment fluid within the inner container, and a fluid applicator carried by the flexible outer container, to communicate with the interior of the outer container, the improvement comprising
   c) a connector having a body defining oppositely projecting third and fourth end portions,
   d) said third and fourth end portions being interfitted with said first and second end portions, respectively, so that said elongated carrier is substantially rigidly joined to said second end portion of the flexible outer container,
   e) whereby pressure may be exerted on a pressure application region of said outer container spaced from said connector body, and sufficient to rupture the inner container, thereby releasing said screening or treatment fluid into the interior of the outer container, enabling fluid migration to the applicator,
   f) and whereby said elongated carrier may be manipulated thereby to manipulate said outer container, and by force transmission via said connector body, to cause said applicator to controllably apply said screening or treatment fluid to said tissue,
   g) said third end portion on said body being endwise interfitted with said first end portion on said elongated carrier, and retained in interfitted condition.

28. The apparatus of claim 27 wherein said fourth end portion on said body is telescopically interfitted with said second end portion in said flexible outer container, and retained in interfitted connection.

29. The apparatus of claim 28 wherein said telescopic interfitting of said fourth end portion on said body with said second end portion on said flexible outer container is established at locations that are everywhere spaced from said pressure application region of said outer container.

30. The apparatus of claim 27 wherein said third end portion on said body is telescopically interfitted with said first end portion on said elongated carrier, and retained in interfitted condition.

31. The apparatus of claim 27 wherein said connector body is molded and has one of the following:
   i) synthetic resinous composition
   ii) elastomer composition
   iii) rubber composition.

32. The apparatus of claim 31 wherein said connector body has opposite end recesses at said third and fourth end portions thereof.

33. The apparatus of claim 27 wherein said screening or treatment fluid consists essentially of one of the following:
   i) an aqueous iodine solution,
   ii) an acetic acid solution,
   iii) podophyllum,
   iv) other fluid for treating living tissue.

34. The apparatus of claim 27 including grip means associated with the connector for enabling releasable endwise gripping connection of at least one of the following:
   i) the connector to the end of the outer container,
   ii) the connector to the end of the carrier.

35. An apparatus for applying screening or treatment fluid to body tissue, said apparatus including:
   a) an elongated carrier, having a first end portion,
   b a flexible outer container having a generally tubular second end portion and a frangible inner container protectively located within the outer container, there being screening or treatment fluid within the inner container, and a fluid applicator carried by the flexible outer container, to communicate with the interior of the outer container, the improvement comprising
   c) a connector having a body defining oppositely projecting third and fourth end portions,
   d) said third and fourth end portions being interfitted with Raid first and second end portions, respectively, so that said elongated carrier is substantially rigidly joined to said second end portion of the flexible outer container,
   e) whereby pressure may he exerted on a pressure application region of said outer container spaced from said connector body, and sufficient to rupture the inner container, thereby releasing said screening or treatment fluid into the interior of the outer container, enabling fluid migration to the applicator,
   f) and whereby said elongated carrier may be manipulated thereby to manipulate said outer container, and by force transmission via said connector body, to cause said applicator to controllably apply said screening or treatment fluid to said tissue,
   g) said connector body being molded and having one of the following:

i) synthetic resinous composition
ii) elastomer composition
iii) rubber composition, h) said connector body having opposite end recesses at said third and fourth end portions thereof,
   i) and wherein said opposite end recesses have cylindrical form and have a relatively smaller diameter at said third end portion, and a relatively larger diameter at said fourth end portion.

36. An apparatus for applying screening or treatment fluid to body tissue, said apparatus including:

a) an elongated carrier, having a first end portion, b) a flexible outer container having a generally tubular second end portion and a frangible inner container protectively located within the outer container, there being screening or treatment fluid within the inner container, and a fluid applicator carried by the flexible outer container, to communicate with the interior of the outer container, the improvement comprising c) a connector having a body defining oppositely projecting third and fourth end portions, d) said third and fourth end portions being interfitted with said first and second end portions, respectively, so that said elongated carrier is substantially rigidly joined to said second end portion of the flexible outer container, e) whereby pressure may he exerted on a pressure application region of said outer container spaced from said connector body, and sufficient to rupture the inner container, thereby releasing said screening or treatment fluid into the interior of the outer container, enabling fluid migration to the applicator, f) and whereby said elongated carrier may be manipulated thereby to manipulate said outer container, and by force transmission via said connector body, to cause said applicator to controllably apply said screening or treatment fluid to said tissue, g) and including a tongue and groove locking means associated with said third and first end portions for blocking separation of said body and carrier after interfitting thereof.

* * * * *